(12) United States Patent
Barthe (10) Patent No.: US 10,226,645 B2
(45) Date of Patent: Mar. 12, 2019

(54) METHODS AND SYSTEMS FOR ULTRASOUND TREATMENT

(71) Applicant: Guided Therapy Systems, LLC, Mesa, AZ (US)

(72) Inventor: Peter G. Barthe, Phoenix, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

(21) Appl. No.: 14/513,251

(22) Filed: Oct. 14, 2014

(65) Prior Publication Data

US 2015/0080771 A1    Mar. 19, 2015

Related U.S. Application Data

(63) Continuation of application No. 13/545,929, filed on Jul. 10, 2012, now Pat. No. 8,858,471.

(60) Provisional application No. 61/506,609, filed on Jul. 11, 2011, provisional application No. 61/506,610, filed on Jul. 11, 2011, provisional application No. 61/506,127, filed on Jul. 10, 2011, provisional
(Continued)

(51) Int. Cl.
| | |
|---|---|
| A61N 7/00 | (2006.01) |
| A61N 7/02 | (2006.01) |
| A61B 18/18 | (2006.01) |
| A61M 37/00 | (2006.01) |
| A61B 18/00 | (2006.01) |

(52) U.S. Cl.
CPC .................. *A61N 7/00* (2013.01); *A61N 7/02* (2013.01); *A61B 18/18* (2013.01); *A61B 2018/00642* (2013.01); *A61M 37/0092* (2013.01); *A61N 2007/0004* (2013.01); *A61N 2007/006* (2013.01); *A61N 2007/0017* (2013.01); *A61N 2007/0034* (2013.01); *A61N 2007/0039* (2013.01); *A61N 2007/0052* (2013.01); *A61N 2007/0073* (2013.01); *A61N 2007/0078* (2013.01); *A61N 2007/027* (2013.01)

(58) Field of Classification Search
CPC ..... A61B 2018/00642; A61M 37/0092; A61N 2007/0004; A61N 2007/0017; A61N 2007/0034; A61N 2007/0039; A61N 2007/0052; A61N 2007/006; A61N 2007/0073; A61N 2007/0078; A61N 2007/027; A61N 7/00; A61N 7/02
See application file for complete search history.

(56) References Cited

U.S. PATENT DOCUMENTS

5,655,539 A * 8/1997 Wang .................. A61B 8/4281
                                                           600/472
6,629,929 B1 * 10/2003 Jago ....................... G10K 11/34
                                                           600/443
(Continued)

*Primary Examiner* — Katherine Fernandez
(74) *Attorney, Agent, or Firm* — Quarles & Brady LLP (57) ABSTRACT

A method and system for ultrasound treatment are provided. Acoustic energy, including ultrasound, can serve as input energy to a mask with apertures, such apertures acting as secondary acoustic sources to create a modulated output acoustic energy in a treatment region and treatment effects. Under proper control output energy can be precisely placed and controlled in tissue. In some embodiments, methods and systems are configured for ultrasound treatment based on creating an output energy distribution in tissue. In some embodiments, methods and systems are configured based on creating an output temperature distribution in tissue.

15 Claims, 9 Drawing Sheets

Related U.S. Application Data application No. 61/506,163, filed on Jul. 10, 2011, provisional application No. 61/506,126, filed on Jul. 10, 2011, provisional application No. 61/506,125, filed on Jul. 10, 2011, provisional application No. 61/506,160, filed on Jul. 10, 2011.

(56) References Cited

U.S. PATENT DOCUMENTS

| | | | |
|---|---|---|---|
| 7,615,016 B2 * | 11/2009 | Barthe | A61B 8/14 600/437 |
| 2003/0229331 A1 * | 12/2003 | Brisken | A61M 37/0092 604/500 |
| 2006/0058664 A1 * | 3/2006 | Barthe | A61N 7/00 600/439 |
| 2006/0074355 A1 * | 4/2006 | Slayton | A61H 23/0245 601/2 |
| 2007/0078290 A1 * | 4/2007 | Esenaliev | A61N 7/00 600/1 |
| 2009/0093737 A1 * | 4/2009 | Chomas | A61N 7/02 601/2 |

* cited by examiner

$$\mathbb{I}(x,y,z,t) \Rightarrow \mathcal{M}(x,y,z,t) \Rightarrow \mathbb{O}(x,y,z,t)$$

Figure 8

METHODS AND SYSTEMS FOR ULTRASOUND TREATMENT

CROSS-REFERENCE TO RELATED APPLICATIONS

This application is a continuation of U.S. patent application Ser. No. 13/545,929 filed Jul. 10, 2012, which claims the benefit of U.S. Provisional Patent Applications 61/506,609 filed Jul. 11, 2011; U.S. 61/506,610 filed Jul. 11, 2011; U.S. 61/506,127 filed Jul. 10, 2011; U.S. 61/506,163 filed Jul. 10, 2011; U.S. 61/506,126 filed Jul. 10, 2011; U.S. 61/506,125 filed Jul. 10, 2011 and U.S. 61/506,160 filed Jul. 10, 2011; all of which are incorporated by reference herein.

BACKGROUND

A variety of methods and systems and methods exist to treat tissue, including mechanical means, lasers and other photon-based sources, radio frequency (RF) electrical currents, microwaves, cryogenic based techniques, and their various combinations, among others.

Each of these modalities has limitations which prevent a high degree of spatial control and precision during treatment. For example, in tissue the extreme absorption and scattering of photons relegates light based therapies to superficial applications that are tissue specific. Typically, electric currents, such as those emitted from a RF source, flow along the path of least impedance and are diffuse and non-selective, with maximum effect to tissue at the source. Further, the centimeter wavelengths of microwaves preclude tight focusing and energy placement in tissue.

Ultrasound can provide depth and precision of energy placement in tissue; however, it has currently been limited in application to either broad planar sources such as used in physiotherapy treatment, or as a single beam of focused sound, which is scanned sequentially over numerous areas, either electronically or mechanically, which is slow. Array based systems which can produce multiple sound beams are cumbersome and expensive and cannot in general produce output energy with a high degree of control or flexibility.

What is needed is an ultrasound treatment method and system that can provide simultaneous multiple beams of controlled energy to produce fractionated intense energy effects, such as thermal effects.

SUMMARY

Methods and systems for ultrasound treatment are provided. Acoustic energy, including ultrasound, under proper functional control can penetrate deeply and be controlled precisely in tissue. In various embodiments, methods and systems can be configured for ultrasound treatment based on creating an input energy distribution, passing it through apertures in a mask, which act in parallel as secondary acoustic sources to create an output distribution function. In various embodiments, methods and systems can be configured to create and control a desired temperature distribution.

Some embodiments provide an ultrasound treatment system configured for temporarily or permanently affecting tissue or its physiology. The ultrasound treatment system can comprise an energy source configured for delivery of acoustic or other energy to a treatment region; a control system for facilitating control of the energy source; and a set of masks, apertures, mask components, input/output, and secondary systems in communication with the control system to define a spatio-temporal distribution of the energy in the treatment region.

Some embodiments provide a method for providing ultrasound treatment. The method can comprise localizing a treatment region; delivering acoustic energy from an energy source into the treatment region; controlling the delivery of acoustic energy; producing at least one treatment effect in the treatment region of interest with the delivering acoustic energy. The method can further comprise monitoring of results of the ultrasound treatment during and/or after of the delivery of acoustic energy. The method can further comprise planning of additional treatment.

DRAWINGS

The present disclosure will become more fully understood from the description and the accompanying drawings, wherein.

DESCRIPTION

The following description is merely exemplary in nature and is in no way intended to limit the various embodiments, their application, or uses. As used herein, the phrase "at least one of A, B, and C" should be construed to mean a logical (A or B or C), using a non-exclusive logical "or," As used herein, the phrase "A, B and/or C" should be construed to mean (A, B, and C) or alternatively (A or B or C), using a non-exclusive logical "or." It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices, in addition, the embodiments may be practiced in any number of industrial or medical contexts and that the various embodiments relating to a method and system for ultrasound treatment as described herein are merely indicative of exemplary applications for the invention. For example, the principles, features and methods discussed may be applied to any industrial or medical application. Further, various aspects of the various embodiments may be suitably applied to cosmetic applications. Moreover, some of the embodiments may be applied to cosmetic enhancement of skin and/or various subcutaneous tissue layers.

According to various embodiments described herein, methods are provided to create tailored space-time acoustic energy distributions in a treatment region. Various embodiments provide controlling delivery of acoustic energy into a treatment region by modulating an input energy distribution with a mask to create an output energy distribution. Since temperature in a targeted portion of a treatment region is proportional to the intensity of acoustic energy that is delivered, various embodiments provide controlling delivery acoustic energy into a treatment region which exceeds a threshold of cell death.

Various embodiments provide an ultrasound system configured for concentration of energy and increased power output to treat tissue in a region of interest. Some embodiments include an ultrasound system comprising a mask, which provides a greater intensity of ultrasound energy from the mask than the intensity the ultrasound intensity from the source. In some embodiments, the intensity of ultrasound energy at the mask can be tuned to different depths or sizes of lesions or shapes by tailoring the size of the aperture and the width of the mask. In some embodiments, the source is the primary source of ultrasound energy and the energy that is output of the mask is the secondary source of energy.

In some embodiments the mask can be cooled to control the tissue temperature in the region of interest. When using the ultrasound system at shallow depths in tissue, the coupling medium fills the apertures. In some embodiments, high-frequency can improve the targeting shallow depths within the tissues of the region of interest, in some embodiments, the primary source provides ultrasound energy to a mask comprising a plurality of apertures which converts the primary energy into a new energy field at the exit of each aperture, which is the secondary source, in some embodiments, the width of the mask can be thicker which can configure the aperture as a waveguide. In some embodiments, the thickness of the mask can tune the energy field of the secondary source.

In some embodiments, the mask may be shaped (i.e. not flat) and can be configured to focus energy to one point. In some embodiments, the ultrasound system comprising mask can create a lesion in a surface of skin. The mask can be configured to create a lesion at a surface of skin in a region of interest. In some embodiments, the ultrasound system can comprise a temperature modulator coupled to or integrated into mask and configured to modulate the temperature of the mask. For example, the temperature of the mask can be modulated using electric currents or Peltier modules. Modulating temperature of the mask can be used to configure the secondary source of energy for treatment of a surface of the skin. Modulating temperature of the mask can be configured for use of a photon-based energy source, which can be a tertiary source of energy. Typically, the mask will absorb acoustic or ultrasound energy such that the mass does not heat by absorbing the ultrasound energy.

Various embodiments provide methods and systems for concentrating sound energy source onto mask of apertures to produce treatment effects. In some embodiments, the apertures can yield greater power output than if aperture area was covered by a transducer alone. The apertures can be varied sizes and shapes to create treatment effects of varied sizes, depths, and shapes. In some embodiments, the acoustic energy can contain one or more frequencies to produce varied sizes, depths, and shapes of treatment.

In some embodiments, the apertures can include auxiliary components, such as, for example, thermal control components. In some embodiments, a coupling medium between sound energy source and mask can be liquid and include thermal, hydraulic, and/or pneumatic control. A liquid coupling medium can be dispensed through apertures to provide external coupling to treatment area. The coupling medium can be temperature controlled.

In some embodiments, the treatment effect can be a thermal effect in tissue in a region of interest. In some embodiments, a treatment effect can be a non-thermal effect in tissue in a region of interest. In some embodiments, a treatment effect can start below the surface or extend to the surface of skin. In some embodiments, sound energy and mask of apertures can vary in three dimensions and/or be time varying.

In some embodiments, the ultrasound treatment system can be combined with ultrasound imaging. In some embodiments, the ultrasound treatment system can be treatment system combined with other imaging, other sensing systems, and/or tissue parameter monitoring systems. In some embodiments, the ultrasound treatment system can be combined with a photon based, RF current, or other energy source.

Various embodiments provide a method for providing ultrasound treatment. In some embodiments, emitting primary ultrasound energy field from primary energy source; directing the primary ultrasound energy field into a plurality of apertures in a mask; converting the primary ultrasound energy field into a plurality of secondary ultrasound energy fields having an increased intensity; delivering the plurality of secondary ultrasound energy fields into a treatment region comprising the tissue; and initiating a thermal effect in the treatment region.

In some embodiments, the method can further comprise monitoring of results of the at least one treatment effect in the treatment region during the delivering the output energy. In some embodiments, the method can further comprise monitoring of results of the at least one treatment effect in the treatment region after the delivering the output energy. In some embodiments, the method can farther comprise planning of additional treatment.

In some embodiments, the at least one treatment effect is a cosmetic enhancement. In some embodiments, the at least one treatment effect is at least one of coagulation, increased perfusion, reduction of inflammation, generation of heat shock proteins, and initiation of healing cascade. In some embodiments, the at least one treatment effect is peaking inflammation in the injury location and initiating a coagulation cascade in at least a portion of the treatment region. In some embodiments, the at least one treatment effect is stimulating collagen growth in a portion of treatment region. In some embodiments, the method can further comprising imaging the treatment region.

Various embodiments provide an ultrasound treatment system. In some embodiments, the system can comprise a primary energy source configured for delivery of primary ultrasound energy field; a mask configured to receive and convert the ultrasound energy into a secondary source configured to provide a secondary ultrasound energy field; and a control system for facilitating control of the primary energy source and the secondary energy source; wherein an intensity of the secondary ultrasound energy field is greater than the intensity of the primary ultrasound energy field.

In some embodiments, the mask comprising a plurality of apertures configured to convert the primary ultrasound energy field into the secondary ultrasound energy field. In some embodiments, the system can further comprise a temperature modulator coupled to the mask and operable to modulate a temperature of the mask.

In some embodiments, the system can further comprise a photon based energy source configured to deliver photon based energy through the secondary energy source and into the treatment region. In some embodiments, the system can further comprise a radio frequency based energy source configured to deliver radio frequency energy through the secondary energy source and into the treatment region. In some embodiments, the output energy is configured to initiate a treatment effect in the treatment region.

Various embodiments provide an ultrasound treatment system, in some embodiments, the system can comprise a primary energy source configured for delivery of primary ultrasound energy field; a mask configured to receive and convert the ultrasound energy into a secondary source configured to provide a secondary ultrasound energy field; and a control system for facilitating control of the primary energy source and the secondary energy source; wherein an intensity of the secondary ultrasound energy field is greater than the intensity of the primary ultrasound energy field.

In some embodiments the thermal effect is one of heating the tissue, or creating a conformal region of elevated temperature in the treatment region. In some embodiments, the thermal effect is one of lesion creation in the region of interest, tissue necrosis in a portion of the treatment region; coagulation tissue in the treatment region, or exceeding a thermal capacity of tissue in a portion of the treatment region, and combinations thereof.

In some embodiments, the method can comprise controlling at least one of the primary energy source and the secondary energy source. In some embodiments, the method can comprise delivering a photon-based energy into the treatment region and imitating a second treatment effect in the treatment region.

In some embodiments, a method can comprise localizing a treatment region; choosing a primary energy source, delivering acoustic input energy from a primary energy source through a plurality of mask apertures to create an output energy; delivering the output energy into the treatment region; and controlling the output energy to produce at least one treatment effect in the treatment region.

Figure 1:
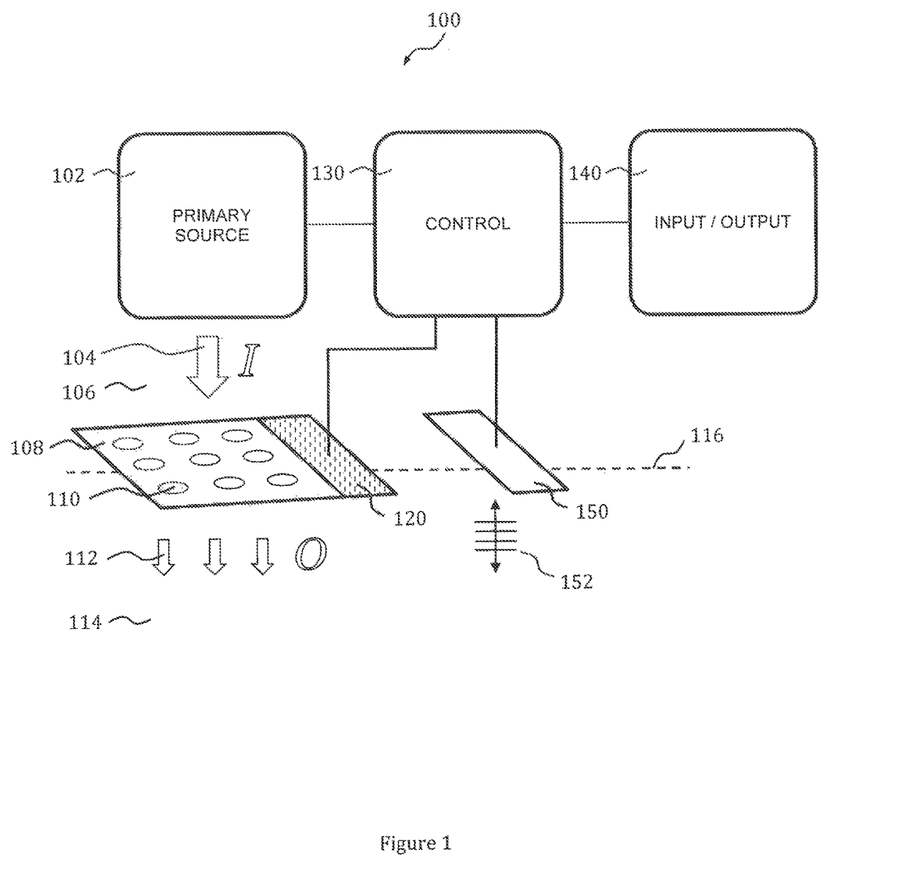
FIG. 1 is a block diagram illustrating an ultrasound treatment system and method, in accordance with various non-limiting embodiments.

With reference to FIG. 1, a method of ultrasound treatment is illustrated. In various embodiments, ultrasound treatment method can comprise localizing a primary energy source 102 and delivering input energy 104 through a coupling medium 106 onto a mask 108 and through apertures 110, which, acting as secondary sources create output energy 112 in a treatment region 114, after passing through potential layers 116. In some embodiments, mask components 120 are mounted upon, adjacent to, or disposed within mask 108 and include passive or active temperature control components. In some embodiments, mask 108 can comprise temperature sensors, contact sensors, pressure sensors, position tracking sensors including optical position sensors, impedance sensors, transducers, absorbers, reflectors, membranes, matching layers, fluid control, hydraulic, and pneumatic components to name a few. Primary energy source 102 and mask components 120 are controlled via control system 130, with associated software and methods. Control system 130 can comprise an input output (I/O) system 140, such as a touch panel, switches, indicators, and audible alarms. In some embodiments secondary systems 150 are also coupled to control system 130, and are configured for ultrasound imaging, therapy and/or monitoring 152, tissue parameter monitoring. In some embodiments, an additional energy source can provide laser or photon based therapies, radio frequency (RF) based therapy. Control system 130 can coupled and/or control impedance monitoring, video monitoring, motion control, and can also include memory devices such as EEPROMs or rechargeable batteries and systems for a portable, hand-held, or wireless ultrasound treatment system. In various embodiments, primary energy source 102 is an ultrasound or other acoustic source. In various embodiments, primary energy source 102 can be composed of single or multiple element cylindrical, spherical, planar, lensed or electronically phased or unfocused acoustic sources or their combination in any geometric configuration, power amplitude, and timing, creating any spatial and temporal distribution of input energy 104. In various embodiments, ultrasound based primary energy source 102 is composed of lead zirconate titanate piezoelectric ceramics or other transducer materials such as lithium niobate. In various embodiments, coupling medium 106 is liquid. In various embodiments, coupling medium 106 is a gel. In various embodiments, coupling medium 106 is a solid. In various embodiments, coupling medium 106 is a gas. In various embodiments, coupling medium 106 is a composite material. In various embodiments, treatment region 114 (or region of interest) comprises a skin surface and subcutaneous tissue below. In various embodiments, treatment region 114 comprises an organ or artificial or engineered tissue. In various industrial embodiments, treatment region 114 can comprise plastic or other materials to be treated by output energy 112. In various embodiments, ultrasound treatment system and method are used extracorporally. In other embodiments, ultrasound treatment system and method are used intracorporally or both.

In various embodiments mask 108 is metal. In various embodiments mask 108 is a composite. In various embodiments, mask 108 is multilayered. In various embodiments, mask 108 can move manually or via motion mechanism or can be exchanged for other masks. In various embodiments, apertures 110 are holes. In various embodiments, coupling medium 106 is solid, apertures 110 are solid and conduct sound, and mask 108 is a void or composed of materials that otherwise do not conduct sound. In various embodiments, mask 108 is covered by a membrane. In various embodiments, apertures 110 are passive or active materials. In various embodiments, apertures 110 are flat or shaped, such as lensed. In various embodiments, apertures 110 are waveguides. In various embodiments, mask 108 partially transmits sound through potential layers 116 into treatment region 114. In various embodiments, mask 108 can absorb sound. In various embodiments, mask 108 can reflect, deflect, and/or diffuse some or all of input energy 104.

In various embodiments, output energy 112 creates a mechanical effect in treatment region 114. For example, a mechanical effect can be any one of or any combination of cavitation, vibration, hydrodynamic, resonance-induced, streaming, vibro-accoustic stimulation, or a pressure gradient. In various embodiments, output energy 112 creates an ablative effect in treatment region 114. For example, an ablative effect can be any one of or any combination of lesion creation, tissue necrosis, coagulation, or exceeding a thermal capacity of tissue, or combinations thereof. In various embodiments, output energy 112 creates a thermal effect in treatment region 114. For example, a thermal effect can be at least one of heating subcutaneous tissue, creating a conformal region of elevated temperature, or creating conformal region of elevated temperature and a second conformal region of elevated temperature, or combinations thereof.

In various embodiments, output energy 112 can trigger (initiate and/or stimulate) one or more bio-effects in treatment region 114. A biological effect can be stimulating or increase an amount of heat shock proteins. Such a biological effect can cause white blood cells to promote healing of a portion of subcutaneous tissue in treatment region 114. A biological effect can be to restart or accelerate the wound healing cascade in treatment region 114 and/or in tissue proximate thereto. A biological effect can be increasing the blood perfusion in treatment region 114 and/or in tissue proximate thereto. A biological effect can be encouraging collagen growth. A biological effect may increase the liberation of cytokines and may produce reactive changes in treatment region 114 and/or in tissue proximate thereto. A biological effect may by peaking inflammation in treatment region 114 and/or in tissue proximate thereto. A biological effect may at least partially shrinking collagen portion in treatment region 114 and/or in tissue proximate thereto. A biological effect may be denaturing of proteins in treatment region 114 and/or in tissue proximate thereto.

A biological effect may be creating immediate or delayed cell death (apoptosis) in treatment region 114 and/or in tissue proximate thereto. A biological effect may be collagen remodeling in treatment region 114 and/or in tissue proximate thereto. A biological effect may be the disruption or modification of biochemical cascades. A biological effect may be the production of new collagen. A biological effect may be a stimulation of cell growth in treatment region 114 and/or in tissue proximate thereto. A biological effect may be angiogenesis. A biological effect may be a cell permeability response. A biological effect may be an enhanced delivery of medicants to treatment region 114 and/or to tissue proximate thereto.

In various embodiments, output energy 112 can initiate and/or stimulate one or more biological responses in treatment region 114, such as, those described herein. For example, a biological response can be at least one of diathermy, hemostasis, revascularization, angiogenesis, growth of interconnective tissue, tissue reformation, ablation of existing tissue, protein synthesis and/or enhanced cell permeability.

Figure 2A:
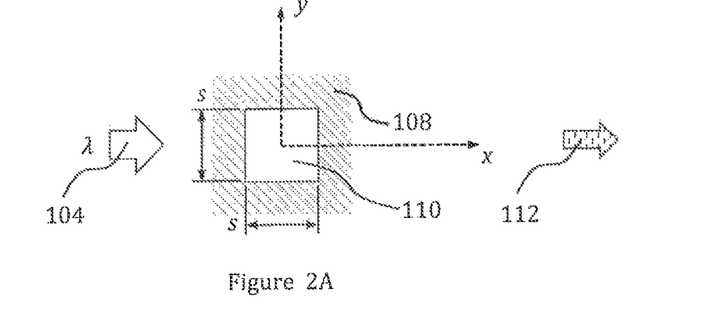
FIG. 2A is a diagram illustrating an ultrasound treatment system mask, in accordance with various non-limiting embodiments.
Figure 2B:
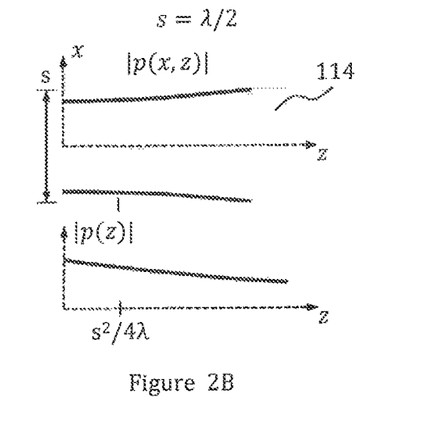
FIGS. 2B-E are a set of graphs each illustrating spatial pressure distributions, in accordance with various embodiments.
Figure 2C:
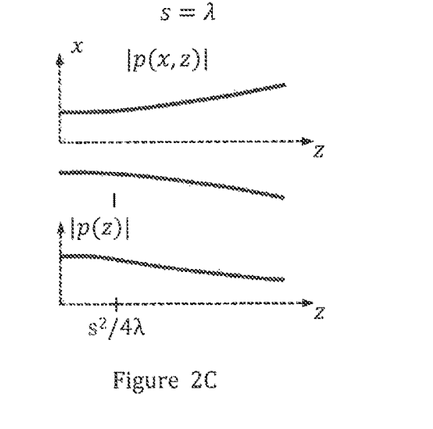
Figure 2D:
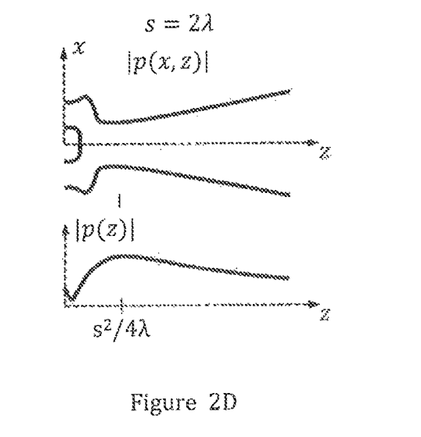
Figure 2E:
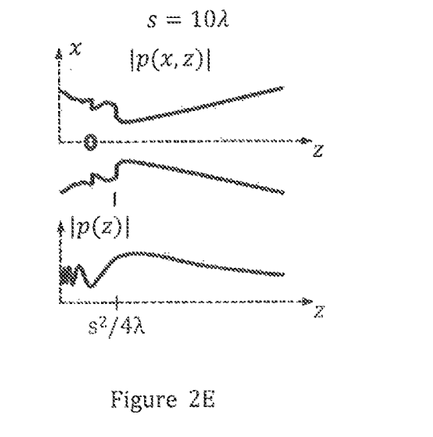
Figure 2F:
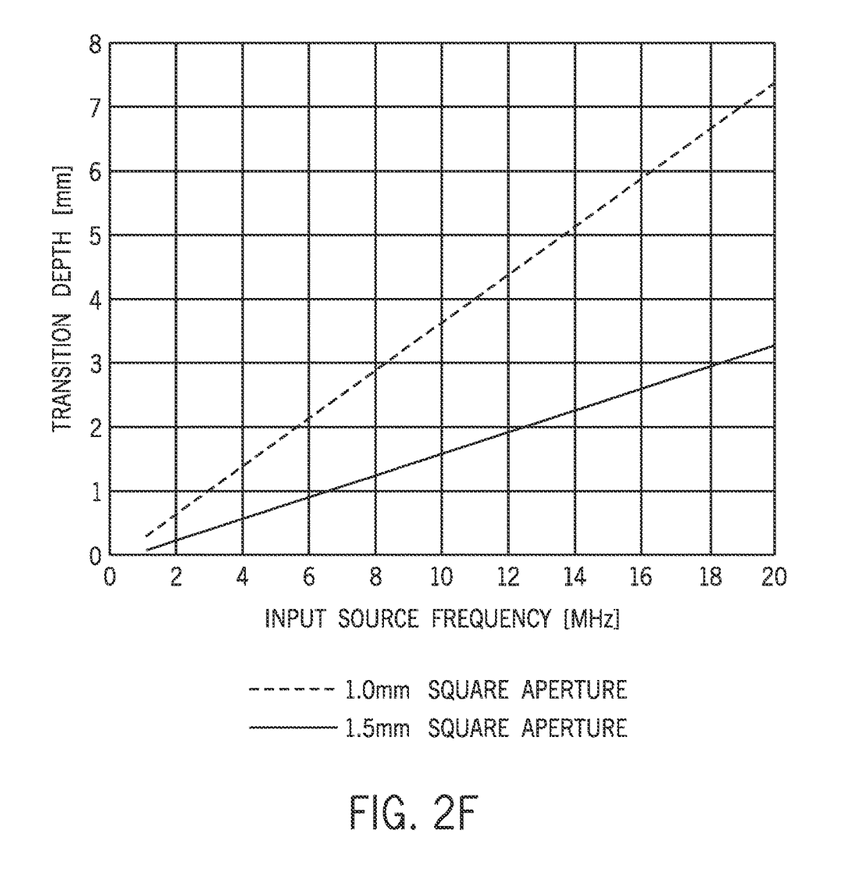
FIG. 2F is a plot illustrating transition depth versus frequency in accordance with various non-limiting embodiments.

With reference to FIG. 2A and according to various embodiments, an ultrasound treatment system, can comprise an input energy 104 of one or more wavelengths lambda, $\lambda$, incident on a mask 108, with apertures 110 of dimensions s per side, thereby creating an output energy 112 in the treatment region 114. Referring now to FIGS. 2B to 2E the spatial distribution of output energy 112, in the treatment region 114 is illustrated from a single aperture 110 as the side, s, of the aperture is increased from $\lambda/2$ to $\lambda$ to $2\lambda$ to $10\lambda$, respectively. For example, acoustically small apertures, i.e. $\lambda \leq 1$, the lateral (along x or y) and axial (along z) normalized pressure magnitude follow a smooth and monotonic contour. However, for acoustically large apertures, $\lambda > 1$, constructive and destructive acoustic interference in the treatment region 114 create a more complex output energy distribution, with an axial peak occurring near the so-called far-field transition distance, $s^2/4\lambda$, for a square aperture of side s, or $a^2/\lambda$ for a circular aperture of radius a. With reference to FIG. 2F, in various embodiments, mask 108, apertures 110, energy source 102, mask components 120, and control system 130 are configured to place the free-field maxima of output energy 112 at a desired depth in the treatment region 114. In various embodiments lensed apertures can further control the acoustic field spatial distribution in the treatment region 114.

Figure 3:
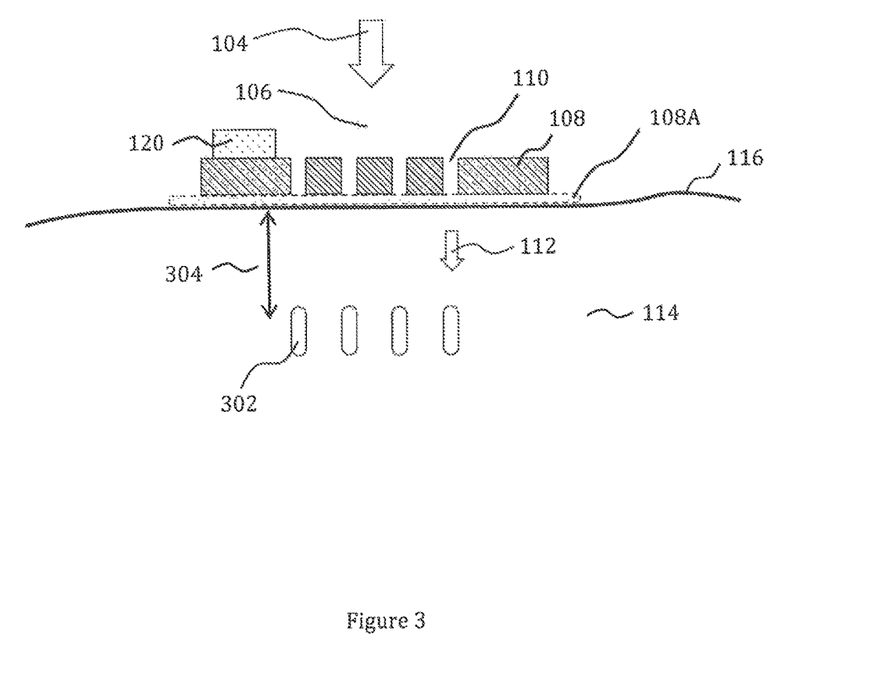
FIG. 3 is a block diagram illustrating various methods and systems of ultrasound treatment, in accordance with various non-limiting embodiments.

Moving to FIG. 3, in some embodiments the input acoustic energy 104, mask 108, and apertures 110 create an output energy 112 creating a treatment effect 302, such as a thermal effect, whose depth 304 in the treatment region 114 is optionally modulated via mask components 120, such as temperature control components. In various embodiments, the desired treatment effect 302 can include the surface. In various embodiments, changing the frequency of input energy 104 is configured to move the position of treatment effect 302 and/or provide multiple depths of treatment effect 302. In various embodiments, mask 108 may include components such as a layers 108A, such as a membrane layer or other layers, with or without apertures 110, which may be used to retain a liquid coupling medium 106. In various embodiments layer 108A is a plastic film. In various embodiments, treatment effect 302 can occur at various angles with respect to mask 108 based on magnitude and phase of input energy 104 at aperture 110. In various embodiments at least one of treatment effect 302 can intersect in the treatment region 114.

Figure 4:
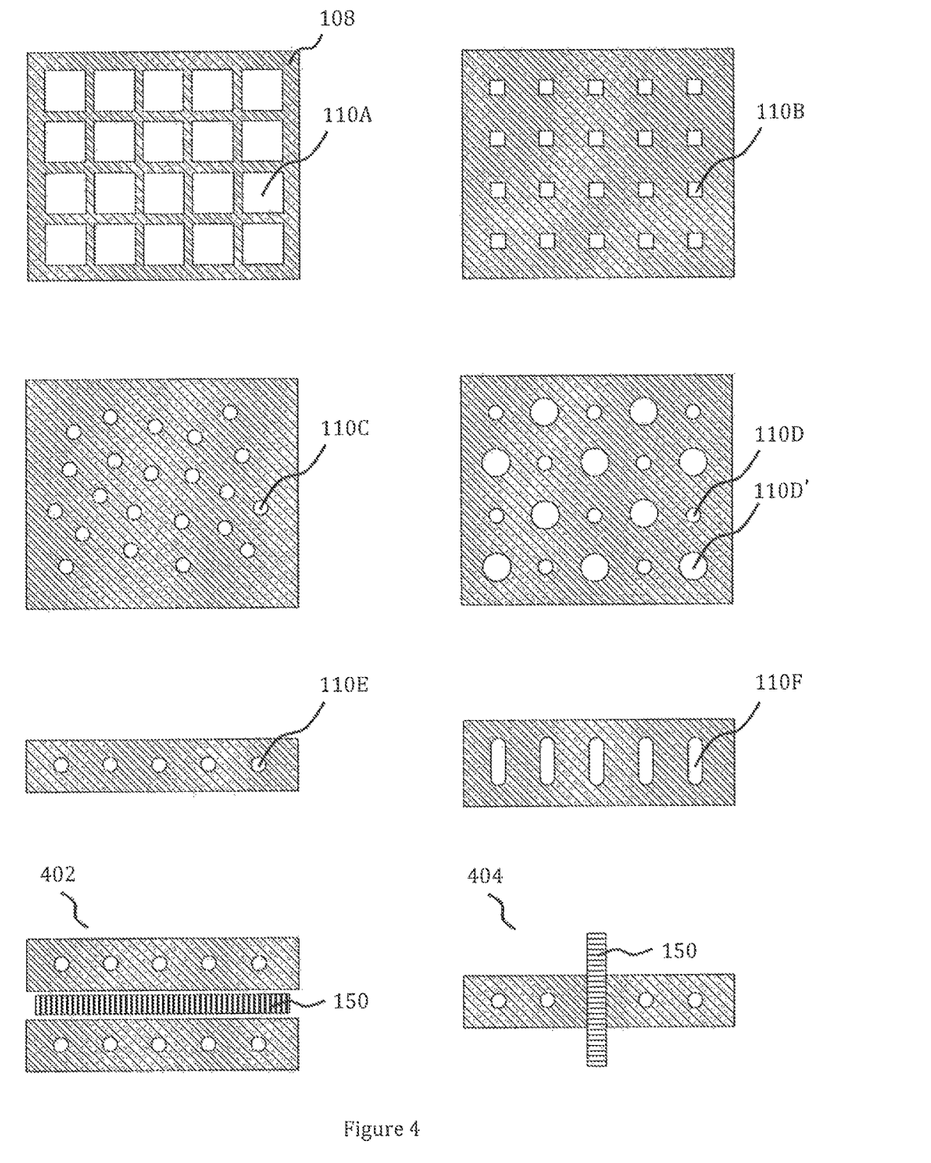
FIG. 4 is a diagram illustrating set of different mask and transducer configurations, in accordance with various non-limiting embodiments.

Various embodiments of masks 108 and apertures 110 are illustrated in FIG. 4. Aperture 110A illustrates a large opening or mesh-like mask 108, while in contrast aperture 110B is more closed, with smaller apertures 110. In various embodiments the relative acoustic spacing between adjacent apertures 110 determines if their output energy 112 combines partially or fully in the treatment region 114 or can be considered as independent sound fields. In some embodiments, apertures 1100 are placed in a random spatial pattern, within bounds, as opposed to a rectilinear or other periodic pattern, and can used to obscure potential treatment side effects, such as temporary edema or erythema on the surface of skin. In various embodiments, mask 108 has multiple sized or shaped apertures, such as apertures 110D and 110D' which can create multiple patterns of output energy 112 in the treatment region 114. In various embodiments, at least two different diameter or sized apertures 110D and 110D' create two different depths of treatment. In various embodiments, at least two different diameter or sized apertures 110D and 110D' create two different sized treatment regions. In various embodiments, mask 108 can consist of a line of apertures 110E or multi-dimensional apertures 110F, such as slots, which can produce different field patterns of output energy 112 along different axes. In various embodiments, mask 402 can be split into more than one zone and secondary systems 150, can be integrated, such as a transducer for an ultrasound imaging and monitoring system. In various embodiments, transducer can be configured in-line along mask 402 or transverse or along the center of a mask 404.

Figure 5:
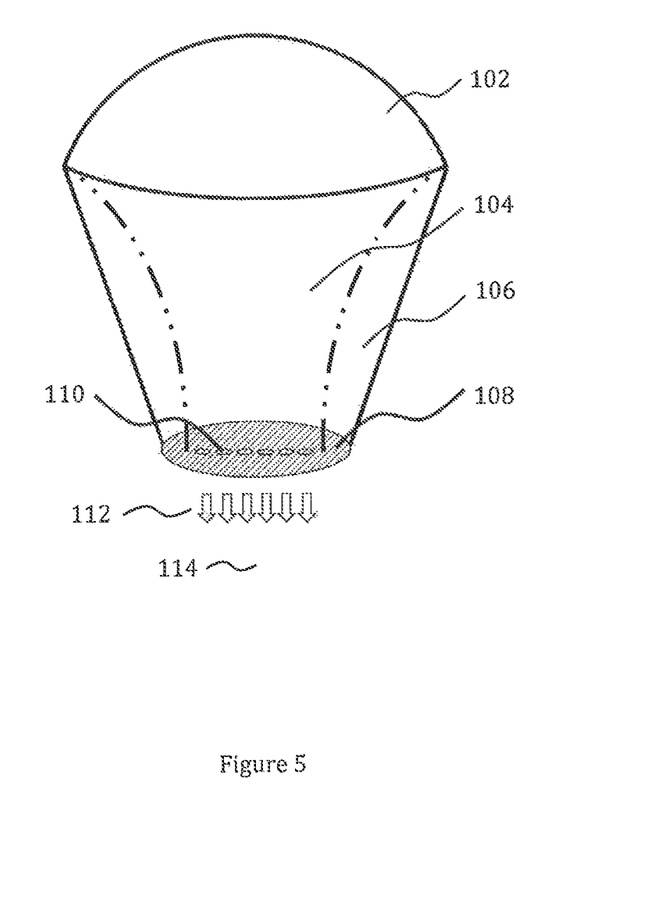
FIG. 5 is a block diagram illustrating an exemplary ultrasound treatment system in accordance with various non-limiting embodiments.

According to various embodiments as illustrated in FIG. 5, the primary energy source 102 is a spherically focused or lensed ultrasound source, which concentrates acoustic input energy 104 emitted from a large surface area (e.g. spherical shell) through an enclosed coupling, medium 106, such as water, onto a mask 108, such as a stainless steel mask, and through apertures 110, to create a pattern of output energy 112 in the treatment region 114. In such embodiments, the level of output energy 112 can be made very intense, even if emitted from a small aperture 110, and such intense sound levels can be exploited in the treatment region 114 for treatment effects 302 such as thermal effects. Such embodiments illustrate that even if the aperture 108 is physically small or acoustically small a large amount of power can be emitted at the aperture 110. Such large power output may not be easily deliverable if a single active transducer element was disposed at aperture 110. In various embodiments, a fluid coupling medium 106 can be held above atmospheric pressure or consist of a material that can avoid cavitation. In various embodiments, a fluid reservoir can be used to maintain the level of coupling medium 106. Various embodiments may be used to output fluid coupling medium 106 to provide external acoustic coupling to treatment region 114.

Figure 6:
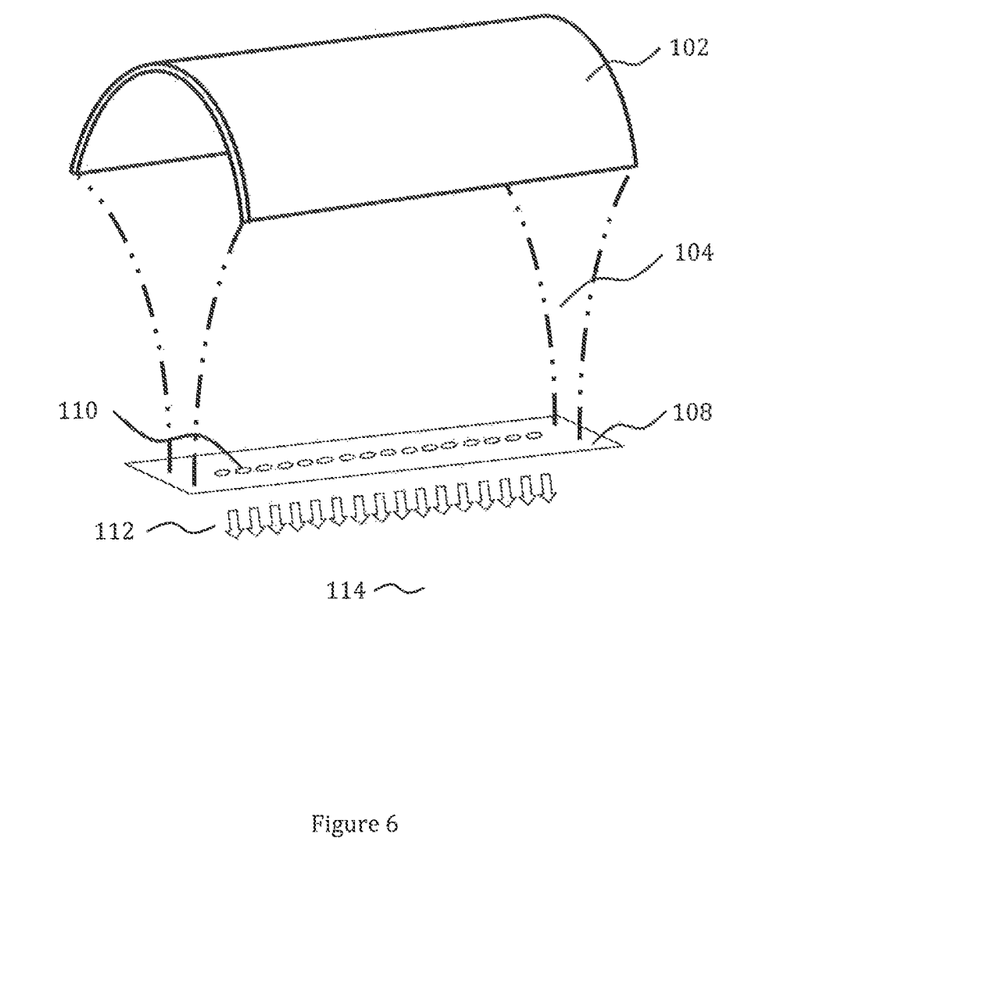
FIG. 6 is a block diagram illustrating an exemplary ultrasound treatment system, in accordance with various non-limiting embodiments.

According to various embodiments and with reference to FIG. 6, the primary energy source is a cylindrically focused ultrasound source, which concentrates acoustic input energy 104 emitted from a large surface area (e.g. cylindrical shell) onto a mask 108 and through apertures 110, to create a pattern of output energy 112 in the treatment region 114. In various embodiments, the primary energy source is a phased array, including phase variation and/or beam steering, and including beamforming over the mask 108 and apertures 110.

Figure 7:
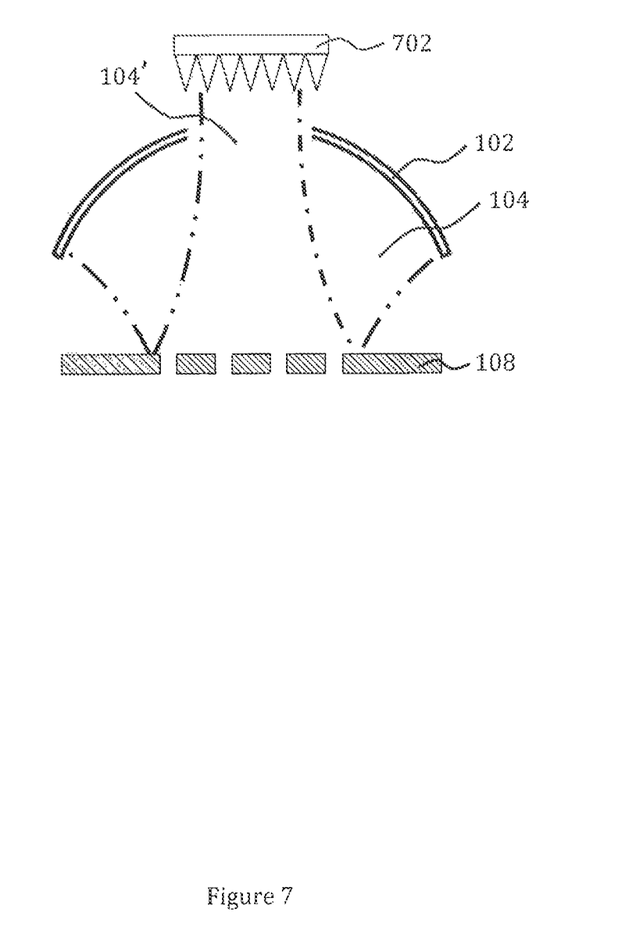
FIG. 7 is a block diagram illustrating an exemplary ultrasound treatment system in accordance with various non-limiting embodiments.

According to various embodiments, as illustrated in FIG. 7, a primary energy source focuses an incident acoustic input energy 104 onto a mask 108, and a portion of such incident acoustic energy 104 is reflected back by such mask 108 as reflected input energy 104' which is then absorbed by an absorber 702. In one embodiment, an opening in the primary energy source can allow the reflected input energy 104' to pass through. In another embodiment, the absorber 702 is on the surface of or in front of the source. In another embodiment the primary source is electrically isolated where the reflected energy impinges on it, such electrically isolated region electronically damped by a network including a resistor, in another embodiment, opening in primary energy source 102 includes plastic tubing which absorbs and attenuates sound while serving as a liquid coupling fluid hydraulic control.

Figure 8:
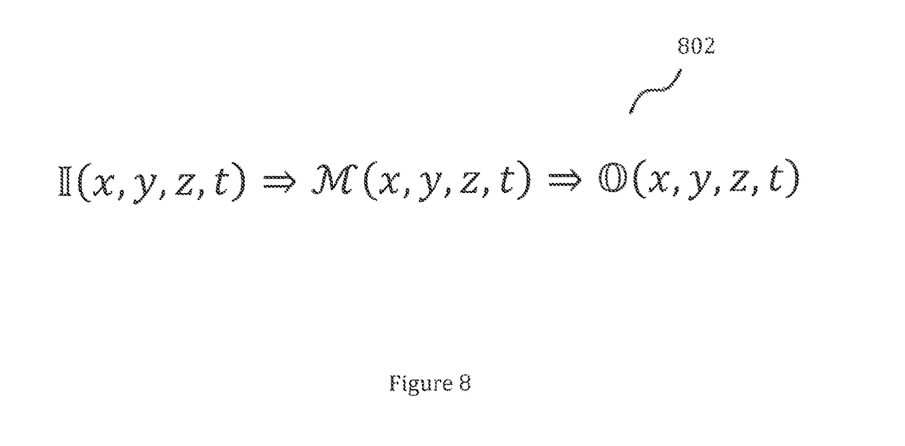
FIG. 8 is a spatio-temporal equation describing various ultrasound fields, in accordance with various non-limiting embodiments.

Moving to FIG. 8, a mathematical relationship 802 encapsulates the ultrasound treatment system as a spatio-temporal input energy 104 distribution function $\mathbb{I}(x, y, z, t)$, which is modulated by a spatio-temporal aperture 110 mask 108 function $\mathbb{M}(x, y, z, t)$ to create a spatio-temporal output energy 112 distribution function $\mathbb{O}(x, y, z, t)$. As such, any acoustic field distribution and timing can be synthesized for the output energy function 112. Of note, in various embodiments mask surface can be three-dimensional and/or time varying.

In various embodiments, ultrasound treatment system 100 is an entire system capable of at least one of treating, imaging, or monitoring, before, during and after treatment, using at least one of acoustic energy and any other energy source, including for example laser, photon emission, and/or radio frequency energy. In one embodiment, ultrasound treatment system 100 comprises acoustic primary energy source 102, control system 130, and at least one other energy source, all encompassed in one unit.

Various embodiments provide a method for providing ultrasound treatment. The method can comprise localizing a treatment region 114, choosing a primary energy source 102, delivering acoustic input energy 104 from the primary energy source 102 through the mask 108 apertures 110 and into the treatment region 114, and controlling the output energy 112 to produce at least one treatment effect 302 in the treatment region 114. The method can further comprise monitoring of results of the ultrasound treatment during and/or after of the delivery of acoustic output energy 112. The method can further comprise planning of additional treatment. In some embodiments, the method is a method of cosmetic enhancement.

The method can comprise providing at least one bio-effect in the in at least one treatment region 114. The method can comprise destroying tissue in the at least one treatment region 114. The method can further comprise generating at least one biological effect in tissue proximate to the at least one treatment region 114. Control of one or more parameters of the output energy 112, defines the explicit shape of the treatment region 114 to affect ultrasound treatment. As will be apparent to those of ordinary skill in the art, output energy 112 can be employed in any method and/or system described herein. It should be appreciated that designated treatment effect 302 has a conformal volume that can be spatially and temporally controlled by ultrasound treatment system 100 and expanded in one or more conformal volumes. Such effect will produce one or more distinct zones of controlled and predictable parameters and dimensions by either electronic and/or mechanical displacements of the acoustic primary energy source, 102 and associated components, mask 108, etc.

As used herein, the term cosmetic enhancement can refer to procedures, which are not medically necessary and are used to improve or change the appearance of a portion of the body. For example, a cosmetic enhancement can be a procedure that is used to improve or change the appearance of a nose, eyes, eyebrows and/or other facial features, or to improve or change the appearance and/or the texture and/or the elasticity of skin, or to improve or change the appearance of a mark or scar on a skin surface, or to improve or change the appearance and/or the content of fat near a skin surface, or the targeting of a gland to improve or change the appearance a portion of the body. Since it is not medically indicated for improving one's physical well-being, cosmetic enhancement is an elective procedure. As used herein, cosmetic enhancement does not diagnose, prevent, treat, or cure a disease or other medical condition. Furthermore, cosmetic enhancement is not a method for treatment of the human or animal body by surgery or therapy and diagnostic methods practiced on the human or animal body. Cosmetic enhancement is a non-surgical and non-invasive procedure. In some embodiments, cosmetic enhancement can be a non-surgical and non-invasive procedure that is performed at home by a user who is not a medical professional.

The following patents and patent applications are incorporated by reference: US Patent Application Publication No. 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No. 20060084891, entitled Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using imaging, Therapy, and Temperature Monitoring Ultrasonic System, issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; and US Patent Application Publication No. 20080281255, entitled "Methods and Systems for Modulating Medicants Using Acoustic Energy" published Nov. 13, 2008.

While the invention has been disclosed herein, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are not intended to be limiting in describing the full scope of systems and methods of this invention. Equivalent changes, modifications and variations of various embodiments, materials, systems, and methods may be made within the scope of the present invention, with substantially similar results.

The invention claimed is:

1. An ultrasound treatment system comprising:
a primary energy source configured for delivery of a first ultrasound energy;
a secondary energy source comprising a plurality of mask apertures configured to receive the first ultrasound energy, wherein the primary energy source is configured to concentrate the first ultrasound energy onto the plurality of mask apertures, wherein a first group of the plurality of mask apertures is configured to receive a first portion of the first ultrasound energy and deliver a first distribution of energy fields to a first depth in a treatment region and a second group of the plurality of mask apertures is configured to receive a second portion of the first ultrasound energy and deliver a second distribution of energy fields to a second depth in the treatment region, wherein the secondary energy source is at least partially reflective and reflects a third portion of the first ultrasound energy; and either the first depth is different than the second depth or the first distribution of energy fields has a different field pattern than the second distribution of energy fields;
an ultrasound absorber that is separate from the primary energy source, the ultrasound absorber configured and positioned to absorb the reflected third portion of the first ultrasound energy; and
an ultrasound emission controller configured to control the emission of the first ultrasound energy from the primary energy source.

2. The system according to claim 1, wherein the secondary energy source is configured to convert the first ultrasound energy into the first and second distributions of energy fields, each having a greater intensity than the primary energy source.

3. The system according to claim 1, further comprising a temperature controller coupled to the second energy source comprising the plurality of mask apertures and operable to control a temperature of the second energy source.

4. The system according to claim 1, further comprising a photon based energy source configured to deliver photon based energy through the secondary energy source and into the treatment region.

5. The system according to claim 1, further comprising a radio frequency based energy source configured to deliver radio frequency energy through the secondary energy source and into the treatment region.

6. The system according to claim 1, further comprising an imaging system configured to image at least a portion of the treatment region.

7. The system according to claim 1, wherein the first group of the plurality of mask apertures is configured to form a first distribution of shaped conformal regions of elevated temperature in the treatment region and the second group of the plurality of mask apertures is configured to form a second distribution of shaped conformal regions of elevated temperature in the treatment region, wherein the first distribution of shaped conformal regions of elevated temperature comprise a different volumetric shape than the second distribution of shaped conformal regions of elevated temperature.

8. The system according to claim 1, wherein the ultrasound emission controller, in use, controls the primary energy source to provide the first distribution of energy fields and the second distribution of energy fields such that at least one of the first distribution of energy fields and the second distribution of energy fields is sufficient to initiate a treatment effect in the treatment region and wherein the treatment effect is heating tissue in the treatment region or creating a conformal region of elevated temperature in the treatment region.

9. The system according to claim 1, wherein the ultrasound emission controller, in use, controls the primary energy source to provide the first distribution of energy fields and the second distribution of energy fields such that at least one of the first distribution of energy fields and the second distribution of energy fields is sufficient to initiate a treatment effect in the treatment region and wherein the treatment effect is selected from the group consisting of:
   a. lesion creation in the treatment region;
   b. tissue necrosis in a portion of the treatment region;
   c. coagulation of tissue in the treatment region;
   d. exceeding a thermal capacity of tissue in a portion of the treatment region;
   e. peaking inflammation in an injury location and a coagulation cascade in at least a portion of the treatment region;
   f. stimulation of collagen growth in a portion of the treatment region;
   g. increased perfusion in the treatment region;
   h. reduction of inflammation in the treatment region;
   i. generation of heat shock proteins in the treatment region;
   j. initiation of a healing cascade in the treatment region; and
   k. combinations thereof.

10. An ultrasound treatment system comprising:
a primary energy source configured for delivery of a first ultrasound energy;
a mask comprising a plurality of apertures configured to receive the first ultrasound energy and convert the first ultrasound energy into a plurality of secondary energy sources, wherein the primary energy source is configured to concentrate the first ultrasound energy onto the plurality of mask apertures, wherein a first group of the plurality of apertures is configured to receive a first portion of the first ultrasound energy and deliver a first distribution of energy fields to a first depth in a treatment region and a second group of the plurality of apertures is configured to receive a second portion of the first ultrasound energy and deliver a second distribution of energy fields to a second depth in the treatment region, wherein either the first depth is different than the second depth or the first distribution of energy fields has a different field pattern than the second distribution of energy fields, wherein the mask is at least partially reflective and reflects a third portion of the first ultrasound energy;

an ultrasound absorber that is separate from the primary energy source, the ultrasound absorber configured and positioned to absorb the reflected third portion of the first ultrasound energy; and an ultrasound emission controller configured to control the primary energy source such that, in use, the first distribution of energy fields is configured to create a thermal effect at the first depth and the second distribution of energy fields is configured to create a non-thermal effect at the second depth.

11. The system according to claim 10, further comprising a temperature controller coupled to the mask and operable to control a temperature of the mask.

12. The system according to claim 10, further comprising:
a. a photon based energy source configured to deliver photon based energy through the mask and into the treatment region; or
b. a radio frequency based energy source configured to deliver radio frequency energy through the mask and into the treatment region.

13. The system according to claim 10, further comprising an imaging system configured to image at least a portion of the treatment region.

14. The system according to claim 10, wherein the plurality of apertures is spaced along a line.

15. The system according to claim 10, wherein the control system, in use, controls the primary energy source and the mask to provide the first distribution of energy fields and the second distribution of energy fields such that at least one of the first distribution of energy fields and the second distribution of energy fields is sufficient to initiate a treatment effect in a tissue in the treatment region, wherein the treatment effect on the tissue is selected from the group consisting of:
a. coagulation of the tissue in the treatment region;
b. increased perfusion;
c. reduction of inflammation;
d. generation of heat shock proteins;
e. initiation of healing cascade;
f. lesion creation in the treatment region;
g. tissue necrosis in a portion of the treatment region;
h. exceeding a thermal capacity of the tissue in a portion of the treatment region;
i stimulating collagen growth in a portion of the tissue in the treatment region;
j peaking inflammation in a portion of the tissue in an injury location and initiating a coagulation cascade in at least a portion of the tissue in the injury location; and
k. combinations thereof.

* * * * *

UNITED STATES PATENT AND TRADEMARK OFFICE
CERTIFICATE OF CORRECTION

PATENT NO. : 10,226,645 B2
APPLICATION NO. : 14/513251
DATED : March 12, 2019
INVENTOR(S) : Peter G. Barthe Page 1 of 1

It is certified that error appears in the above-identified patent and that said Letters Patent is hereby corrected as shown below:

In the Specification

Column 4, Line 61, "farther" should be --further--.

Column 8, Line 12, "or a²" should be --or α²--.

Column 8, Line 12, "radius a" should be --radius α--.

Column 9, Line 6, "e.g. spherical" should be --e.g. a spherical--.

Signed and Sealed this
Seventh Day of April, 2020

Andrei Iancu
*Director of the United States Patent and Trademark Office*